United States Patent [19]
Komala

[11] Patent Number: 5,470,163
[45] Date of Patent: Nov. 28, 1995

[54] FOLDING LOTION APPLICATOR

[76] Inventor: Ernest Komala, 375 Wildberry La., Bartlett, Ill. 60103

[21] Appl. No.: 283,288

[22] Filed: Jul. 29, 1994

[51] Int. Cl.$^6$ ................................................ A45D 34/00
[52] U.S. Cl. ........................... 401/126; 401/122; 401/130
[58] Field of Search ................................ 401/126, 130, 401/122

[56] References Cited

U.S. PATENT DOCUMENTS

| 1,602,551 | 10/1926 | Ramsey | 401/130 |
| 4,433,928 | 2/1984 | Kingsford | 401/122 |
| 4,869,612 | 9/1989 | Mooney et al. | 401/130 |

FOREIGN PATENT DOCUMENTS

| 847952 | 7/1939 | France | 401/130 |

*Primary Examiner*—Steven A. Bratlie
*Attorney, Agent, or Firm*—James J. Conlon

[57] ABSTRACT

A collapsible applicator adapted to be folded into a convenient, thin and elongated size to be placed into a bottle of fluid such as tanning lotion and then absorb the lotion whereupon after removal of the applicator from the container it may be expanded in an umbrella like fashion to provide a handle, an elongated, central frame member attached to applicator members extending outwardly therefrom in such a fashion that the user may apply lotion without ever touching the lotion.

7 Claims, 1 Drawing Sheet

FOLDING LOTION APPLICATOR

BACKGROUND OF THE INVENTION (1) Field of the Invention

This disclosure pertains to hand held applicators used to apply lotion, creams, medications and the like to a person's body. In particular, this disclosure shows a collapsible applicator that may be collapsed and inserted into any bottle, attached to the cap, carried with the bottle, and, when needed for use, removed from the container, unfolded and used to apply fluid within the container to virtually any portion of the user's body.

(2) Description of the Prior Art

The prior art shows applicators such that disclosed in the Scuderi, U.S. Pat. No. 4,571,106 (1986) in which the lotion is carried within a customized container and then dispensed with a roll on type ball. The device has a specific curvature to allow it to be hand held and yet reach all parts of the body. There is no hint or suggestion that a collapsible applicator such as the device shown herein is to be used.

Another prior art product is shown in the Brown, U.S. Pat. No. 4,299,005 (1983) in which lotion is carried in a sponge pivotally attached to a handle having telescoping parts to thereby allow the length of the handle to be adjusted to reach various parts of the body. The device is not collapsible and cannot be adapted to fit various containers that contain fluid to be used.

Yet another prior art device is shown in the Kales, U.S. Pat. No. 4,483,356 (1984) which shows a hand held device having a telescoping handle with a lotion dispensing pad pivotally attached at the end of the handle. There is no disclosure in this patent showing or suggesting a collapsible device that may be carried inside the container that has the lotion or other fluid being dispensed.

Another lotion dispensing device is shown in the Meyer, U.S. Pat. No. 4,483,636 (1984) which shows a specialized lotion carrying dispenser into which the lotion must be added to be dispensed. Once the lotion is inside the device, the tubular handle may be squeezed to force out fluid. This patent does not disclose or suggest the combination disclosed by this invention which allows the applicator to be adapted to fit the lotion containers and does not require the user to carry around a separate container for dispensing the lotion or other similar fluid.

SUMMARY

This invention relates to applicators for applying lotions, creams, medicines and the like to a person's body. In the past it was common practice when applying such lotions to merely shake or pour the lotion directly from the container onto one's hand and rub on one's body. This practice presents certain practical and aesthetic problems. Namely, the lotion gets all over the user's hands and may pick up sand, dirt and the like. Additionally, the lotion is not always applied evenly to the person's body since either certain parts cannot be seen or cannot be reached by the person's hand.

Other solutions to the above situations have been proposed as shown in the patents discussed above. In each instance with the patents discussed, it is necessary for the person using the patented device to carry two dispensers, namely, one for the lotion, cream or medicine, and, the second container as shown in these patents. These problems are eliminated or greatly reduced by the present invention that is discussed in this disclosure. The lotion applicator shown herein can easily be adapted to fit into many lotion containers, be stored neatly therein until needed, and then removed, expanded and used. When use is completed, the user simply collapses the applicator, inserts it back into the lotion container and closes the container. At no time does the user contact the lotion with his hands.

In operation, the applicator has a collapsible mechanism which opens and closes in an umbrella like fashion. When stored within the lotion container the applicator resembles a closed umbrella with the applicators nestled alongside a centrally located frame member. In such a position, the applicator elements are in contact with the lotion. When the applicator assembly is removed a linkage mechanism is manually operated by merely shaking the unit to allow two sponge like members soaked with lotion to fall away from the central frame member and thus be in position to apply the carried lotion to the desired part of the user's body.

It is thus an object of the invention to provide a collapsible lotion dispenser that may easily be adapted to fit into many existing lotion dispensing bottles.

It is another object of the invention to provide a lotion applying mechanism that can easily be operated between an open position for applying lotion and a collapsed position for insertion into the lotion container in such a fashion to be easily carried with the container.

It is another object of the invention to provide a lotion applying member that may be easily stored in a collapsed position within a lotion container, and, extended by moving suddenly or shaking to allow application of the lotion without the need for the user to touch the lotion with his/her hands.

It is yet another object of the invention to provide a collar member adapted to be fitted into a lotion container and thus function as a guide for the lotion dispensing mechanism to prevent the lotion dispenser from accidentally getting caught in the container.

It is yet another object of the invention to provide a lotion applying mechanism having a connector for attaching the mechanism to the cap of a lotion container.

These and other objects of the invention will become apparent to those having ordinary skill in the art with reference to the following drawings, description and claims.

DESCRIPTION OF THE PREFERRED EMBODIMENT

Figure 1:
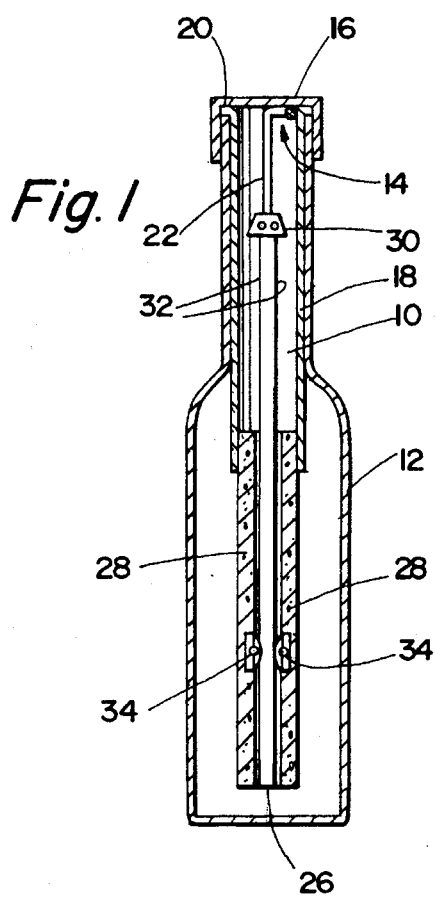
FIG. 1 is a sectional view of a container with the applicator in the collapsed position.
Figure 4:
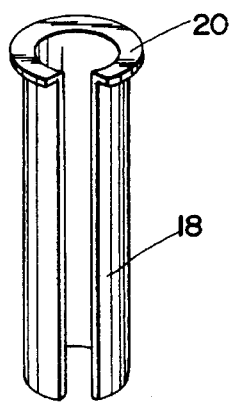
FIG. 4 is a pictorial illustration of the collar.

Referring now to the drawings and in particular to FIG. 1 there is shown a lotion applicator indicated generally by the number 10. The applicator 10 is positioned within the container 12 through opening 14. A cap 16 is shown closing off the opening 14. A guide tube 18 is inserted into the opening 14 and includes a flange portion 20 to prevent the guide 18 from moving into the container 12. As noticed in FIG. 4, the guide tube 18 is a thin plastic member having a rounded, formed configuration that will allow it to be inserted into various size container openings. As noticed in FIG. 1, the guide tube 18 has a length sufficient to extend into the container 12 to keep the applicator 10 in the collapsed position while it is in the container. This feature prevents the applicator 10 from inadvertently opening while in the container which could prevent its ease of removal.

The applicator 10 has a central frame member 22 extending from a connecting loop 24 that attaches to the cap 16 at one end and a hinge member 26 at the other end. A pair of applicator arms 28 are pivotally attached to the hinges 26. A slider member 30 is positioned to move along the central frame member 22 and has a pair of links 32 pivotally attached thereto and extending to pivot pins 34 on the applicator arms 28.

Figure 2:
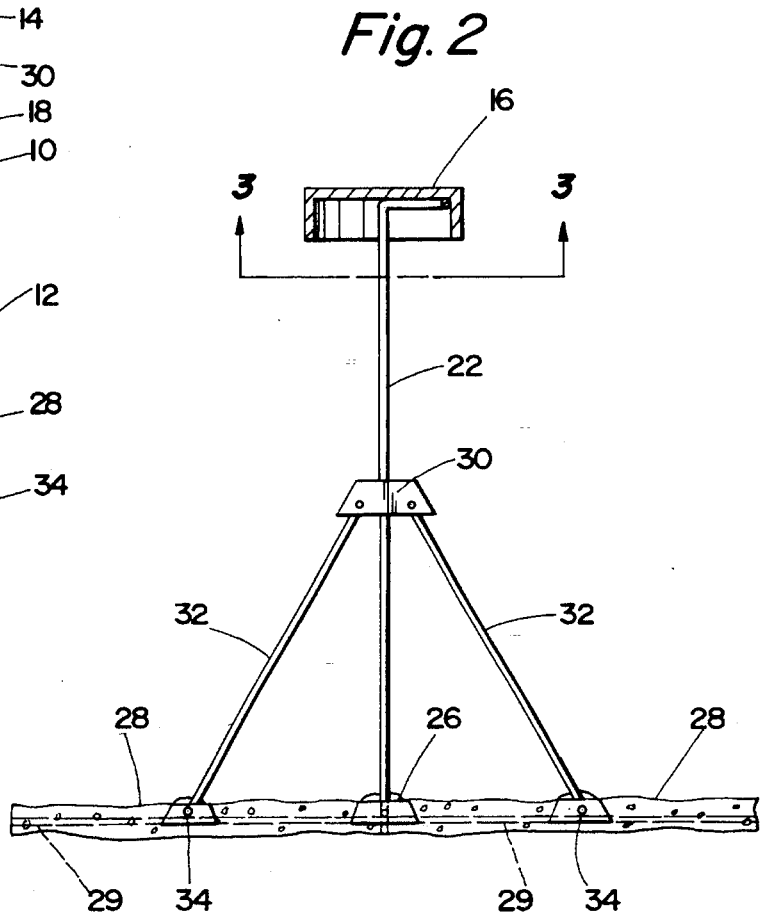
FIG. 2 is a view of the applicator in the extended position.
Figure 3:
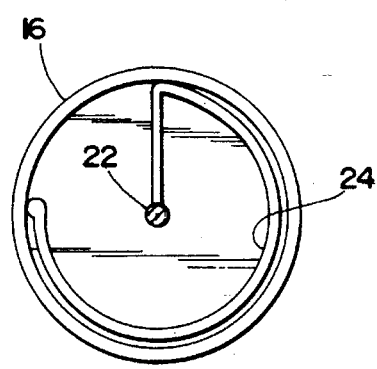
FIG. 3 is a section view taken along lines 3—3 of FIG. 2.

Thus it is noticed that when the applicator assembly 10 is in the extended position shown in FIG. 2 it may be easily inserted into the container 12 merely by having the user position the hinge 26 at the opening 14 and pushing it through the opening 14 and through the guide tube 18 and into the position shown in FIG. 1. When in the position of FIG. 1 the applicator arms 28 are held in the collapsed position and prevented from opening in the container due to the guide tube 18 that extends far enough into the container to prevent the applicator mechanism from opening while in the container. The guide tube 18 is preferably a thin plastic member that can easily be cut and customized to fit into a variety of containers.

The applicator arms 28 are preferably made from a sponge like or absorbent material so that when in contact with the lotion or other fluid in the container 12 the lotion will be retained on the arms as the applicator 10 is removed from the container.

The applicator 10 can be supplied as a kit and sold and marketed separately from the lotion and container. The applicator can be easily attached to a variety of container caps 16 by use of the flexible, adjustable loop 24.

Thus it has been shown by the foregoing that the disclosure shows a lotion applicator that is collapsible and can be easily adapted to a variety of containers and eliminates the need for having two separate containers for the lotion and one for the dispensing of the lotion.

The above description is intended to enable a person having ordinary in the art to practice the invention; however, the invention is not to be limited to the specific features disclosed since one may be able to make modification to the disclosed invention without escaping from the scope of the invention.

What is claimed is:

1. A collapsible applicator for spreading a fluid such as lotions and creams to a person's body, wherein the fluid is carried in a container having at least one opening, the improvement comprising:

a central frame member having grasping means at one end and fluid holding means at the other end for carrying said fluid;

a mechanism for folding and collapsing said fluid holding means into a generally parallel configuration relative to the central frame member to allow the applicator to be easily placed into said container to contact the fluid within the container and then be removed, unfolded and applied to a person's body to apply said fluid without the user's hands coming in contact with said fluid;

said fluid holding means including at least two elongated, porous, sponge like members with means extending outwardly from said central frame member when the applicator is unfolded to apply fluid.

2. The applicator of claim 1, and further including;

tubular guide means having neck means adapted to be positioned within said container carrying said fluid to thereby direct said frame member and mechanism into said container to provide contact between said fluid holding means and the fluid.

3. The applicator of claim 2 wherein said tubular guide means includes:

a flexible, spring-like plastic member having a generally circular configuration and having side edges adapted to overlap and thereby provide said tubular guide means with the feature of providing a multitude of diameters as needed to conform to the size of various container openings.

4. The tubular guide means of claim 3, and:

said flexible plastic member having a flange to fit adjacent said opening of the container to thereby prevent said guide means from inadvertently entering said container.

5. The applicator of claim 1, wherein said fluid to be applied to the body is carried in a container having an open end and said open end having an associated closure member, and;

said grasping means including means for attaching said applicator to said closure member whereby upon attachment and removal of said closure member the applicator will also be positioned within and removed from said container.

6. The applicator of claim 1, and said mechanism for folding said fluid holding means including:

a slider member positioned on said central frame member;

link means attached to said fluid holding means and to said slider member and adapted to fold and unfold said fluid holding means as the slider is moved along said central frame member.

7. A kit for removing viscous product from a container, said container having an open end providing access to said product within the container and having closure means for attachment to said container to seal and close off said open end, said kit comprising:

an applicator;

said applicator having a first end with grasping means for attaching to said closure means and adapted to fit adjacent said open end of said container and said applicator having a second end adapted to fit within said container;

movable arm means with hinge means attached and having product contacting means to contact and carry said viscous product adhering thereto as the applicator is removed from the container;

tubular guide means having stop means to allow the guide means to be easily inserted into said container to a predetermined length to prevent excess movement of said movable arm means within said container that would prevent or interfere with removal of the applicator from the container.

* * * * *